(12) United States Patent
Scherer et al.

(10) Patent No.: US 9,744,168 B2
(45) Date of Patent: Aug. 29, 2017

(54) METHOD OF REDUCING FACIAL FLUSHING ASSOCIATED WITH SYSTEMIC USE OF PHOSPHODIESTERASE TYPE 5 INHIBITORS

(71) Applicant: Galderma Laboratories, Inc., Forth Worth, TX (US)

(72) Inventors: Warren J. Scherer, Pittsburgh, PA (US); Arthur Clapp, Colleyville, TX (US); Philippe Andres, Peymeinade (FR)

(73) Assignee: GALDERMA LABORATORIES, INC., Fort Worth, TX (US)

( * ) Notice: Subject to any disclaimer, the term of this patent is extended or adjusted under 35 U.S.C. 154(b) by 0 days.

(21) Appl. No.: 14/344,099

(22) PCT Filed: Oct. 12, 2012

(86) PCT No.: PCT/IB2012/002500
§ 371 (c)(1),
(2) Date: Mar. 11, 2014

(87) PCT Pub. No.: WO2013/057579
PCT Pub. Date: Apr. 25, 2013

(65) Prior Publication Data
US 2014/0343067 A1    Nov. 20, 2014

Related U.S. Application Data

(60) Provisional application No. 61/548,844, filed on Oct. 19, 2011.

(51) Int. Cl.
| | |
|---|---|
| *A61K 31/165* | (2006.01) |
| *A61K 31/498* | (2006.01) |
| *A61K 31/137* | (2006.01) |
| *A61K 31/4164* | (2006.01) |
| *A61K 31/4174* | (2006.01) |

(52) U.S. Cl.
CPC .......... *A61K 31/498* (2013.01); *A61K 31/137* (2013.01); *A61K 31/165* (2013.01); *A61K 31/4164* (2013.01); *A61K 31/4174* (2013.01)

(58) Field of Classification Search
CPC .................................................. A61K 31/165
See application file for complete search history.

(56) References Cited

U.S. PATENT DOCUMENTS

| | | |
|---|---|---|
| 3,968,219 A | 7/1976 | Rahtz et al. |
| 4,011,322 A | 3/1977 | Rahtz et al. |
| 4,285,967 A | 8/1981 | Gubernick et al. |
| 5,910,312 A | 6/1999 | Fried |
| 6,117,871 A | 9/2000 | Maurer et al. |
| 7,345,065 B2 | 3/2008 | Gil et al. |
| 7,439,241 B2 | 10/2008 | DeJovin et al. |
| 8,410,102 B2 | 4/2013 | Graeber et al. |
| 8,426,410 B2 | 4/2013 | DeJovin et al. |
| 8,513,247 B2 | 8/2013 | Graeber et al. |
| 8,513,249 B2 | 8/2013 | Graeber et al. |
| 8,859,551 B2 | 10/2014 | DeJovin et al. |
| 9,034,830 B2 | 5/2015 | Nanduri et al. |
| 2002/0032201 A1 | 3/2002 | Olejnik et al. |
| 2004/0242588 A1 | 12/2004 | Dejovin |
| 2005/0020600 A1 | 1/2005 | Scherer |
| 2006/0264515 A1 | 11/2006 | Dejovin et al. |
| 2009/0061020 A1 | 3/2009 | Theobald et al. |
| 2009/0304826 A1 | 12/2009 | Lane |

FOREIGN PATENT DOCUMENTS

| | | |
|---|---|---|
| GB | 1589585 | 5/1981 |
| GB | 1594852 | 8/1981 |
| WO | 89/11851 A1 | 6/1989 |
| WO | 95/10280 A1 | 4/1995 |
| WO | 97/04764 A1 | 1/1997 |
| WO | 00/23066 A2 | 4/2000 |
| WO | 00/61144 A1 | 10/2000 |
| WO | 01/13955 A1 | 3/2001 |
| WO | 03/030813 A2 | 4/2003 |
| WO | 2009/082452 A1 | 7/2009 |
| WO | WO2009152344 | 12/2009 |
| WO | WO 2009152344 A2 * | 12/2009 ........... A61K 31/137 |

OTHER PUBLICATIONS

Vyawahare, N., et al. "Effect of novel synthetic evodiamine analogue on sexual behavior in male rats." J. Chem. Bio. (2011), pp. 1-19.*
Drugs.com. "Brimonidine." (c) Jan. 17, 2007. Available from: < http://web.archive.org/web/20070117173703/http://www.drugs.com/cdi/Brimonidine.html >.*
Berge, S. "Pharmaceutical Salts." J. Pharm. Sci. (Jan. 1977), vol. 66, No. 1, pp. 1-19.*
Tong, W-Q. "Salt Screening and Selection: New Challenges and Considerations in the Modern Pharmaceutical R&D Paradigm." Novartis Pharmaceutical Corporation. (Jul. 17, 2006). Available from: < http://pharmacy.utah.edu/pharmaceutics/pdf/Salt.pdf >.*
Neeraj S Vyawahare et al., "Effect of novel synthetic evodiamine analogue on sexual behavior in male rats," Journal of Chemical Biology, Oct. 4, 2011, vol. 5, No. 1, pp. 35-42.
Nielsen et al., Postjunctional α2-adrenoceptors mediate vasoconstriction in human subcutaneous resistance vessels, Br. J. Pharmacol., 1989, 97, 829-834.
Rebora, A., The Management of Rosacea, Am. J. Clin. Dermatol. 2002.3(7), 489-496.
Robin, A., Short-term Effects of Unilateral 1% Apraclonidine Therapy, Arch Ophthalmol, vol. 106, Jul. 1988.
Shanler et al., Successful Treatment of the Erythema and Flushing of Rosacea Using a Topically Applied Selective α1-Adrenergic Receptor Agonist, Oxymetazoline, Arch Dermatol, vol. 143, No. 11, Nov. 2007.

(Continued)

*Primary Examiner* — Noble Jarrell
*Assistant Examiner* — John S Kenyon
(74) *Attorney, Agent, or Firm* — Hoffmann & Baron, LLP

(57) ABSTRACT

The present invention relates to a method of reducing cutaneous facial flushing caused by systemic use of phosphodiesterase type 5 (PDE5) inhibitors by topical facial dermatological application of an effective dose of a composition comprising at least one alpha adrenergic receptor agonist.

8 Claims, No Drawings

(56) References Cited

OTHER PUBLICATIONS

Sibenge et al., Rosacea: A study of clinical patterns, blood flow, and the role of Demodex folliculorum, J. Am. Acad. Dermatol. 1992, 26:590-3.
Spada et al., Differential Effects of α-Adrenoceptor Agonists on Human Retinal Microvessel Diameter, Journal of Ocular Pharmacology and Therapeutics, vol. 17, No. 3, 2001.
Uva et al., Cutaneous Manifestations of Systemic Lupus Erythematosus, Autoimmune Diseases, vol. 2012, Article ID 834291, 15 pages, doi:10.1155, 2012.
Walters, T., Development and Use of Brimonidine in Treating Acute and Chronic Elevations of Intraocular Pressure: A Review of Safety, Efficacy, Dose Response, and Dosing Studies, Survey of Ophthalmology, vol. 41, Supplement 1, Nov. 1996.
Wilkin et al., Standard classification of rosacea: Report of the National Rosacea Society Expert Committee on the Classification and Staging of Rosacea, J. Am. Dermatol. Apr. 2002, No. 4, 46:584-7.
Zuber, T., Rosacea: Beyond First Blush, Hospital Practice, 1997, 32:2, 188-189.
Dorland's Illustrated Medical Dictionary, 28th Edition, 1994, pp. 576-577.
Alphagan 0.5% Ophthalmic Solution (Allergan) Approval: Clinical Pharmacology & Biopharmaceutics, 5228231 D, pp. 1-18, Mar. 13, 1997.
Van Landuyt et al., "Traitement De La Rosacée", Ann. Dermatol. Venerol., 124:729, 1997.
Physicians' Desk Reference, 56th Edition, 2002.
Remington, Joseph P., The Science and Pharmacy, Mack Publishing Company, 1995, Easton, Pennsylvania 18042, pp. 1517-1518 and 1577-1591.
Moore, Alison, Draft Clinical Study Report, Brimonidine Tartrate (COL-118-BAPK-101), pp. 1-5, 2007.
Acheampong et al., Effect of Ocular Dose on the Systemic Absorption and Disposition of Brimonidine in Humans, Pharmaceutical Research, Official Journal of the American Assoc. of Pharmaceutical Scientists, vol. 11, No. 10, S-350, 1994.
Brimonidine Tartarate 0.15% Ophthalmic Solution with Purite Preservation, Center for Drug Evaluation and Research, Application No. 21-262, pp. 1-46, Jun. 29, 2000.
Solution, 0.1% (Brimonidine Purite) Product (Proposed Brand Name): Alphagan, Center for Drug Evaluation and Research, Application No. 21-770, pp. 1-8, May 27, 2004.
Scruggs, et al., the teardrop sign: a rare dermatological reaction to brimonidine, Br. J. Ophthalmol, 2000 84: 667-672.
Scherer, Warren J., U.S. Appl. No. 10/626,037, Prosecution History.
Kibbe, Arthur H., Editor, Handbook of Pharmaceutical Excipients, Third Edition, 2000, pp. 79-82.
Goodman et al., Goodman & Gilman's The Pharmacological Basis of Therapeutics, 10th Edition, 2001, pp. 1795-1848.
Barry, Brian W., Dermatological Formulations—Percutaneous Absorption, University of Bradford, West Yorkshire, England, Marcel Dekker, Inc., pp. 1-126.
Alphagan 0.5% Ophthalmic Solution (Allergan), Approval Letter, Not-Approvable Letter, 5228231 A, Mar. 13, 1997.
Solution, 0.15% Brimonidine Tartarate Ophthalmic Solution, Center for Drug Evaluation and Research, Application No. 21-764, Feb. 4, 2005.
Acheampong et al., Measurement of brimonidine concentrations in human plasma by a highly sensitive gas chromatography/mass spectrometric assay, Journal of Pharmaceutical and Biomedical Analysis, 13 (1995) 995-1002.
Adkins et al., Brimonidine A Review of its Pharmacological Properties and Clinical Potential in the Management of Open-Angle Glaucoma and Ocular Hypertension, Drugs and Aging Mar. 1998: 12(3): 225-241.
Bill et al., Ocular Effects of Clonidine in Cats and Monkeys (*Macaca irus*), Exp. Eye. Res. (1975) 21, 481-488.
Blount et al., Rosacea: A Common, Yet Commonly Overlooked, Condition, American Family Physician, Aug. 1, 2002, vol. 66, No. 3, pp. 435-440.
Borbujo et al., Postjunctional Alpha-1 and Alpha-2 Adrenoceptors in Human Skin Arteries. An in Vitro Study, The Journal of Pharmacology and Experimental Therapeutics, vol. 249, No. 1, pp. 284-287.
Burke et al., Preclinical Evaluation of Brimonidine, Survey of Ophthalmology, vol. 41, Supplement 1, Nov. 1996, pp. S9-S18.
Chotani et al., Silent α2c-adrenergic receptors enable cold-induced vasoconstriction in cutaneous arteries, Am. J. Physiol. Heart Circ. Physiol, 278: H1075-H1083, 2000.
Cross, et al., Transdermal Penetration of Vasoconstrictors—Present Understanding and Assessment of the Human Epidermal Flux and Retention of Free Bases and Ion-Pairs, Pharmaceutical Research, vol. 20, No. 2, Feb. 2003, pp. 270-274.
Cunliffe et al., Clonidine and facial flushing in rosacea, British Medical Journal, Jan. 8, 1977, p. 105.
Decauchy, et al., Rosacea, Pilosebaceous Follicle Pathology, Rev. Prat. (Paris) 1993, 43, 18, pp. 2344-2348.
Flavahan, The Role of Vascular α2-Adrenoceptors as Cutaneous Thermosensors, Int. Union Physiol. Sci./Am. Physiol. Soc., vol. 6, Dec. 1991, pp. 251-255.
Fuchs et al., Heat, but not mechanical hyperalgesia, following adrenergic injections in normal human skin, Pain 90 (2001) 15-23.
Grosshans, E., La rosacee (Rosacea), La Presse Medicale, Dec. 17, 1988, 17, No. 45, pp. 2393-2398.
Grosshans et al., Rilmenidine in rosacea: a double-blind study versus placebo, Ann. Dermatol. Venereal., 1997, 124, 687-691.
Guarrera et al., Flushing in Rosacea: A Possible Mechanism, Archives of Dermatological Research (1982) 272:311-316.
Hornqvist et al., Adrenoceptor-mediated responses in human skin studied by iontophoresis, British Journal of Dermatology (1984) III, 561-566.
Jasper et al., Ligand Efficacy and Potency at Recombinant α2 Adrenergic Receptors, Biochemical Pharmacology, vol. 55, pp. 1035-1043, 1998.
Langer et al., Recent developments in noradrenergic neurotransmission and its relevance to the mechanism of acton of certain antihypertensive agents, Hypertension 1980, 2:372-382.
Lewis et al., Topical Therapies for Glaucoma: What Family Physicians Need to Know, American Family Physician, Apr. 1, 1999, 59(7): 1871-1879.
Ma et al., The Efficacy of 0.2% Brimonidine for Preventing Intraocular Pressure Rise Following Argon Laser Trabeculoplasty, Korean J. Ophthalmol., vol. 13:78-84, 1999.

\* cited by examiner

METHOD OF REDUCING FACIAL FLUSHING ASSOCIATED WITH SYSTEMIC USE OF PHOSPHODIESTERASE TYPE 5 INHIBITORS

This application claims priority based on an International Application filed under the Patent Cooperation Treaty, PCT/IB2012/002500, filed Oct. 12, 2012, which claims priority from U.S. Provisional Application No. 61/548,844, filed Oct. 19, 2011, each of which are incorporated herein by reference.

BACKGROUND OF THE INVENTION

Phosphodiesterase Type 5 (PDE5) inhibitors such as sildenafil (VIAGRA), vardenafil (LEVITRA), and tadalafil (CIALIS) are current treatments for erectile dysfunction. A significant side effect of PDE5 inhibitors is cutaneous facial flushing. Due to this side effect, there is a need to reduce cutaneous facial flushing associated with the use of PDE5 inhibitors.

SUMMARY OF THE INVENTION

The invention relates generally to a method of reducing cutaneous facial flushing associated with systemic use of phosphodiesterase type 5 inhibitors in a human, the method comprising topically administering to the facial skin affected by the cutaneous facial flushing of the human a composition comprising at least one alpha adrenergic receptor agonist and a topically acceptable carrier, in an amount effective to reduce the cutaneous facial flushing.

In one embodiment, the composition comprises at least one alpha-1 adrenergic receptor agonist.

In another embodiment, the composition comprises at least one alpha-2 adrenergic receptor agonist.

In another embodiment, the alpha adrenergic receptor agonist is selected from a group consisting of oxymetazoline, tetrahydrozoline, nephazoline, xylometazoline, phenylepherine, methoxamine, mephentermine, metaraminol, desglymidodrine, midodrine, brimonidine, and the pharmaceutically acceptable salts thereof, and any combination of such compounds or salts.

In another embodiment, the alpha adrenergic receptor agonist is selected from a group consisting of oxymetazoline, tetrahydrozoline, nephazoline, xylometazoline, phenylepherine, methoxamine, mephentermine, metaraminol, desglymidodrine, midodrine, the pharmaceutically acceptable salts thereof, and any combination of such compounds or salts.

In another embodiment, the at least one alpha adrenergic receptor agonist or pharmaceutically acceptable salts thereof is selected from the group consisting of brimonidine, oxzymetazoline, or pharmaceutically acceptable salts thereof, or a combination of any such compounds or salts.

In another embodiment, the only pharmaceutically active compound for reducing cutaneous facial flushing associated with systemic use of phosphodiesterase type 5 inhibitors are brimonidine or a pharmaceutically acceptable salt thereof or oxymetazoline or a pharmaceutically acceptable salt thereof; or a combination of brimonidine or a pharmaceutically acceptable salt thereof and oxymetazoline or a pharmaceutically acceptable salt thereof.

In another embodiment, the only pharmaceutically active compound of any kind in the composition is brimonidine or a pharmaceutically acceptable salt thereof or oxymetazoline or a pharmaceutically acceptable salt thereof; or a combination of brimonidine or a pharmaceutically acceptable salt thereof or oxymetazoline or a pharmaceutically acceptable salt thereof.

In yet another embodiment, the pharmaceutically acceptable salt is oxymetazoline hydrochloride.

In yet another embodiment, the pharmaceutically acceptable salt is brimonidine tartrate.

In yet another embodiment, the alpha adrenergic receptor agonist is the only compound that reduces cutaneous facial flushing in humans.

DETAILED DESCRIPTION OF THE INVENTION

The present invention relates to methods of reducing cutaneous facial flushing in a human wherein the cutaneous facial flushing is associated with, e.g., caused by or resulting directly or indirectly from, the systemic use of PDE 5 inhibitors. Cutaneous facial flushing associated with the systemic use of PDE 5 inhibitors result in undesirable facial redness.

The method comprises topically administering a composition comprising an effective amount of an active compound or pharmaceutically acceptable salt thereof to the facial skin area affected by the cutaneous facial flushing. Active compounds include oxymetazoline, tetrahydrozoline, nephazoline, xylometazoilne, phenylepherine, methoxamine, mephentermine, metaraminol, desglymidodrine, midodrine, brimonidine; the pharmaceutically acceptable salts thereof, or any combination of such compounds and/or salts. The active compounds and their pharmaceutically acceptable salts are commercially available, or can be synthesized by methods well known in the art.

Reduction of cutaneous facial flushing means a noticeable reduction in redness. Preferably, the reduction results in significant restoration of the facial color to that before the administration of a PDE5 inhibitor, and more preferably total restoration of the facial color to that before the administration of a PDE5 inhibitor.

A PDE5 inhibitor is defined as any drug used to block PDE 5 mediated degradation of cyclic GMP in smooth muscle cells lining blood vessels supplying blood to the penis. Such PDE5 inhibitors include, but are not limited to, sildenafil (VIAGRA), vardenafil (LEVITRA), and tadalafil (CIALIS). PDE5 inhibitors are used as treatments for erectile dysfunction.

Brimonidine is 5-bromo-6-(2-imidazolidinylideneamino) quinoxaline. Its structure is shown below.

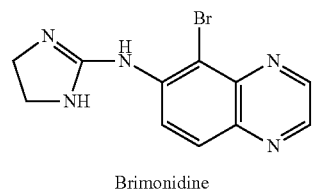 [SMILES: Brc1c(NC2=NCCN2)ccc2nccnc12]

Brimonidine

The structure of oxymetazoline is shown below.

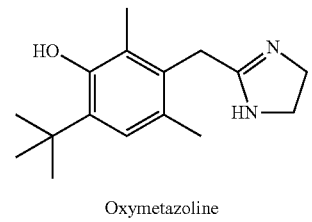 [SMILES: Cc1cc(C(C)(C)C)c(O)c(C)c1CC1=NCCN1]

Oxymetazoline

Pharmaceutically acceptable salts thereof, as used herein, include those salts that are safe and effective for topical use in mammals and that possess the desired biological activity. Pharmaceutically acceptable salts include, for example, acid addition salts of basic groups present in alpha adrenergic receptor agonists useful in the method of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, aspartate, methanesulfonate, ethanesulfonate, benzensulfonate, p-toluenesulfonate and pamoate (i.e., 1,1'-methylene-bis-(2-hydroxy-3-naphthoate)) salts. Other pharmaceutically acceptable salts are described in Berge et al., 66 J. Pharm. Sci. 66, 1-19 (1977).

The syntheses of the active compounds suitable for reducing cutaneous facial flushing associated with the systemic use of PDE 5 inhibitors described above are known in the art. For example, brimonidine or a pharmaceutically acceptable salt thereof and oxymetazoline or a pharmaceutically acceptable salt thereof can be synthesized by methods described in U.S. Pat. No. 7,439,241 and in Fuhrhop, et al. "Organic Synthesis: Concepts and Methods," page 237-238 (2003).

Pharmaceutically Acceptable Carriers

In one embodiment, the compounds of the invention are delivered to the affected area of the skin by a composition comprising a pharmaceutically acceptable topical carrier. As used herein, a pharmaceutically acceptable composition is any composition that can be applied to the skin surface for topical delivery of a pharmaceutical or medicament. Topical compositions of the invention may be prepared according to well-known methods in the art. For example, an active compound that reduces cutaneous facial flushing associated with systemic use of PDE5 inhibitor may be combined with a topical carrier by methods provided in standard reference texts, such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997).

The topical carriers useful for topical delivery of compounds of the invention can be any pharmaceutically acceptable carrier known in the art for topically administering pharmaceuticals. Some examples of topical carriers include solvents, such as a polyalcohol or water; suspensions; emulsions (either oil-in-water or water-in-oil emulsions), such as creams, ointments, or lotions; micro emulsions; gels; liposomes; or powders.

Emulsions and Gels as Topical Carriers

In a preferred embodiment, the topical carrier used to deliver a compound of the invention is an emulsion, e.g., a cream, lotion, or ointment; or a gel. An emulsion is a dispersed system comprising at least two immiscible phases, one phase dispersed in the other as droplets, usually ranging in diameter from 0.1 μm to 100 μm. An emulsifying agent is optionally included to improve stability. When water is the dispersed phase and an oil is the dispersion medium, the emulsion is termed a water-in-oil emulsion. When an oil is dispersed as droplets throughout an aqueous phase as droplets, the emulsion is termed an oil-in-water emulsion. Both are useful as carriers in the methods of the present invention. Emulsions, such as creams, ointments and lotions, that can be used as topical carriers and their preparation are disclosed in REMINGTON: THE SCIENCE AND PRACTICE OF PHARMACY 282-291 (Alfonso R. Gennaro ed. 19th ed. 1995).

In one embodiment, the pharmaceutically acceptable carrier is a gel. Gels are semisolid systems that contain suspensions of inorganic particles, usually small inorganic particles, or organic molecules, usually large organic molecules, interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are known in the art, and may be two-phase or single-phase systems. Some examples of suitable gels are disclosed in REMINGTON: THE SCIENCE AND PRACTICE OF PHARMACY 1517-1518 (Alfonso R. Gennaro ed. $19^{th}$ ed. 1995). Other suitable gels for use with the invention are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002).

Gelling agents, that may be used include those known to one skilled in the art, such as hydrophilic and hydroalcoholic gelling agents frequently used in the cosmetic and pharmaceutical industries. A suitable hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STA-BILEZE®" (ISP Technologies, Wayne, N.J.).

"CARBOPOL®" is one of numerous cross-linked acrylic acid polymers that are given the general adopted name carbomer. "Carbomer" is the USP designation for various polymeric acids that are dispersible but insoluble in water. When the acid dispersion is neutralized with a base a clear, stable gel is formed. The preferred carbomer is Carbomer 934P because it is physiologically inert and is not a primary irritant or sensitizer. Other carbomers include 910, 940, 941, and 1342.

Carbomers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other suitable gelling agents include hydroxyethylcellulose, cellulose gum, MVE/MA decadiene crosspolymer, PVM/MA copolymer, or a combination thereof.

In one embodiment, the minimum amount of gelling agent in the composition is about 0.5%, more preferably, about 0.75%, and most preferably about 1%. In another preferred embodiment, the maximum amount of gelling agent in the composition is about 2%, more preferably about 1.75%, and most preferably about 1.5%.

In another embodiment, the topical carrier used to deliver a compound of the invention is an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995).

The pharmaceutical carrier may also be a cream. A cream is an emulsion, i.e., a dispersed system comprising at least two immiscible phases, one phase dispersed in the other as droplets usually ranging in diameter from 0.1 µm to 100 µm. An emulsifying agent is typically included to improve stability.

The pH of the pharmaceutical carrier is adjusted with, for example, a base such as sodium hydroxide or potassium hydroxide; or an amine base, such as trimethylamine. The pH can also be adjusted with an acid, such as hydrochloric acid or acetic acid. In one embodiment, the minimum pH of the carrier is about 5, preferably 5.5, and most preferably 6.2 when the carrier is diluted by a factor of ten. The maximum pH of the carrier is about 8, preferably about 7.5, more preferably 7, and most preferably about 6.8 when the carrier is diluted by a factor of ten. Each minimum pH value can be combined with each maximum pH value to create various pH ranges. For example, the pH may be a minimum of 6.2 and a maximum of 7.5.

The pH values given above are those that occur if the composition is diluted with water by a factor of ten. It is not necessary to dilute the composition by a factor of ten in order to obtain a pH value. In practice, the composition may be diluted by any value that permits pH to be measured. For example, the composition may be diluted by a factor of about five to about twenty.

Aqueous Topical Compositions of the Invention

In another embodiment, the topical carrier used in the topical compositions of the invention is an aqueous solution or suspension, preferably, an aqueous solution or suspension. Solutions and suspensions are well-known suitable topical carriers for use in the invention. Suitable aqueous topical compositions for use in the invention are disclosed in REMINGTON: THE SCIENCE AND PRACTICE OF PHARMACY 1563-1576 (Alfonso R. Gennaro ed. 19th ed. 1995). Other suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002).

Tonicity-adjusting agents can be included in the aqueous topical compositions of the invention. Examples of suitable tonicity-adjusting agents include, but are not limited to, sodium chloride, potassium chloride, mannitol, dextrose, glycerin, and propylene glycol. The amount of the tonicity agent can vary widely depending on the composition's desired properties. In one embodiment, the tonicity-adjusting agent is present in the aqueous topical composition in an amount of from about 0.5 to about 0.9 weight percent of the composition.

The viscosity of aqueous solutions of the invention can be any convenient viscosity, and can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose. In one embodiment, the aqueous topical compositions of the invention have a viscosity in the range of from about 15 cps to about 25 cps.

In a preferred embodiment, the aqueous topical composition of the invention is an isotonic saline solution, optionally comprising a preservative, such as benzalkonium chloride or chlorine dioxide, a viscosity-adjusting agent, such as polyvinyl alcohol, and/or a buffer system such as sodium citrate and citric acid, or potassium acetate and acetic acid.

Excipients

The topical compositions of the invention can further comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), including, but not limited to, protective agents, adsorbents, demulcents, emollients, preservatives, antioxidants, moisturizers, buffering agents, solubilizing agents, and surfactants. Excipients are non-active and non-essential ingredients in the composition that do not materially affect the basic characteristics of the composition.

Suitable protective agents and adsorbents include, but are not limited to, dusting powders, zinc stearate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

Suitable preservatives include, but are not limited to, parabens, phenoxyethanol, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Chlorine dioxide ($ClO_2$), preferably, stabilized chlorine dioxide, is a suitable preservative for use with topical compositions of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995) discloses a form of stabilized chlorine dioxide and a method for producing same, which can be used as a preservative for aqueous solutions and is useful in topical compositions of the invention. The manufacture or production of certain stabilized chlorine dioxide products is described in U.S. Pat. No. 3,278,447. A commercially available stabilized chlorine dioxide that can be utilized in the practice of the present invention is the proprietary stabilized chlorine dioxide of BioCide International, Inc. of Norman, Okla., sold under the trademark Purogene™ or Purite™ Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Additional Pharmaceutical Active Compounds

In one embodiment, the only pharmaceutically active compound effective in reducing cutaneous facial flushing associated with systemic use of PDE5 inhibitor in the composition is oxymetazoline, tetrahydrozoline, nephazoline, xylometazoilne, phenylepherine, methoxamine, mephentermine, metaraminol, desglymidodrine, midodrine, brimonidine, or a pharmaceutically acceptable salts thereof, or any combination of such compounds or salts. In another embodiment, the only pharmaceutically active compound effective in reducing cutaneous facial flushing associated with systemic use of PDE5 inhibitor is oxymetazoline, tetrahydrozoline, nephazoline, xylometazoilne, phenylepherine, methoxamine, mephentermine, metaraminol, desglymidodrine, midodrine, and the pharmaceutically acceptable salts thereof, and any combination of such compounds or salts. In yet another embodiment, the only pharmaceutically active compound effective in reducing cutaneous facial flushing associated with systemic use of a PDE5 inhibitor is brimonidine, or a pharmaceutically acceptable salts thereof, or oxymetazoline or a pharmaceutically acceptable salt thereof. In still another embodiment, the only two pharmaceutically active compound effective in reducing cutaneous facial flushing associated with systemic use of PDE5 inhibitor in the composition are brimonidine or a pharmaceutically acceptable salt thereof and oxymetazoline or a pharmaceutically acceptable salt thereof.

In a further embodiment, the only active compound of any kind in the composition is oxymetazoline, tetrahydrozoline, nephazoline, xylometazoilne, phenylepherine, methoxamine, mephentermine, metaraminol, desglymidodrine, midodrine, brimonidine, or a pharmaceutically acceptable salts thereof, or any combination of such compounds or salts. In another embodiment, the only active compound of any kind is oxymetazoline, tetrahydrozoline, nephazoline, xylometazoilne, phenylepherine, methoxamine, mephentermine, metaraminol, desglymidodrine, midodrine, and the pharmaceutically acceptable salts thereof, and any combination of such compounds or salts. In yet another embodiment, the only active compound of any kind in the composition is brimonidine, or a pharmaceutically acceptable salts thereof, or any combination of such compounds or salts. In still another embodiment, the only two active compounds of any kind in the composition are brimonidine or a pharmaceutically acceptable salt thereof and oxymetazoline or a pharmaceutically acceptable salt thereof.

In another embodiment, one or more additional pharmaceutically active ingredients are included in the compositions of the invention. Additional active ingredients may include any pharmaceutically active ingredient. For example, the one or more additional pharmaceutically active ingredients may include, but are not limited to, antibacterial agents, anthelmintic agents, antioxidant agents, steroidal anti-inflammatory agents, non-steroidal anti-inflammatory agents, antiangiogenic agents, and derivatives of retinoic acid.

Dosage

Dosages and dosing frequency of an effective amount of the compounds of the invention can be determined by trained medical professionals, typically during pre-clinical and clinical trials. The dosages and dosing frequency depend on numerous factors, such as the activity of the compounds of the invention, the characteristics of the particular topical composition, and the identity and severity of the cutaneous facial flushing associated with systemic use of PDE5 inhibitor being treated.

In general, the active compounds described above are present in a composition of the invention in a minimum amount of about 0.01%, 0.05%, 0.1%, 0.15%, 0.2%, 0.25%, 0.3%, 0.35%, 0.4%, or 0.5% based upon the total weight of the composition. Generally, the active compounds described above are present in a composition of the invention in a maximum amount of about 5% 4%, 3%, 2%, 1%, 0.9%, 0.8%, 0.7%, or 0.6% based upon the total weight of the composition. For example, some suitable dosages of brimonidine tartrate are 0.07%, 0.18%, and 0.5%.

Topical Administration

The pharmaceutical compositions of the invention may be applied directly to the affected area of the skin in any manner known in the art. For example, a solution may be applied by cotton swab or may be sprayed. A suspension or an emulsion may be applied with a q-tip or an applicator stick, or by simply spreading a composition of the invention onto the affected area with one or more fingers. Preferably, the pharmaceutical compositions of the invention is applied only to skin, and is not administered to eyes.

Generally the amount of a topical composition of the invention applied to the affected skin area ranges from about 0.0001 $g/cm^2$ of skin surface area to about 0.01 $g/cm^2$, preferably, 0.001 $g/cm^2$ to about 0.003 $g/cm^2$ of skin surface area. Typically, one to four applications per day are recommended during the term of treatment.

Miscellaneous Definitions

It is to be understood that the present invention contemplates embodiments in which each minima is combined with maxima to create all feasible ranges. For example, either (1) brimonidine or a pharmaceutically acceptable salt thereof or (2) oxymetazoline or a pharmaceutically acceptable salt thereof may be present in a composition of the invention in an amount of from about 0.01 percent to about 5 percent based upon the total weight of the composition, preferably, from about 0.1 percent to about 1 percent based upon the total weight of the composition, or more preferably, from about 0.1 percent to about 0.5 percent based upon the total weight of the composition.

EXAMPLES

Example 1a

Gel Composition

| Ingredient | Weight Percent |
| --- | --- |
| tetrahydrozoline | 0.18% |
| Carbomer 934P | 1.25% |
| Methylparaben | 0.2% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 1b

Gel Composition

| Ingredient | Weight Percent |
| --- | --- |
| Oxymetazoline hydrochloride | 0.2% |
| Carbomer 934P | 1.25% |

-continued

| Ingredient | Weight Percent |
|---|---|
| Methylparaben | 0.2% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 1c

Gel Composition

| Ingredient | Weight Percent |
|---|---|
| naphazoline acetate | 0.18% |
| Oxymetazoline hydrochloride | 0.2% |
| Carbomer 934P | 1.25% |
| Methylparaben | 0.2% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 2a

Cream Composition

| Ingredient | Weight Percent |
|---|---|
| Xylometalozine tartrate | 0.5% |
| Phenoxyethanol | 0.8% |
| Methylparaben | 0.2% |
| Propylparaben | 0.05% |
| Disodium EDTA | 0.01% |
| Butylated Hydroxytoluene | 0.05% |
| PEG-300 | 4.0% |
| PEG-6 Stearate (and) Glycol Stearate (and) PEG-32 Stearate | 7.5% |
| Cetostearyl alcohol | 4.0% |
| Caprylic capric triglycerides | 7.0% |
| Diisopropyl adipate | 7.0% |
| Oleyl alcohol | 7.0% |
| Lanolin USP | 2.0% |
| Ceteareth-6 (and) Stearyl Alcohol | 2.0% |
| Ceteareth-25 | 2.0% |
| Tartaric Acid | 0.001% |
| DI Water | 55.389% |
| TOTAL | 100% |

Example 2b

Cream Composition

| Ingredient | Weight Percent |
|---|---|
| Oxymetazoline hydrochloride | 0.5% |
| Phenoxyethanol | 0.8% |
| Methylparaben | 0.2% |
| Propylparaben | 0.05% |
| Disodium EDTA | 0.01% |
| Butylated Hydroxytoluene | 0.05% |
| PEG-300 | 4.0% |
| PEG-6 Stearate (and) Glycol Stearate (and) PEG-32 Stearate | 7.5% |
| Cetostearyl alcohol | 4.0% |
| Caprylic capric triglycerides | 7.0% |
| Diisopropyl adipate | 7.0% |
| Oleyl alcohol | 7.0% |
| Lanolin USP | 2.0% |
| Ceteareth-6 (and) Stearyl Alcohol | 2.0% |
| Ceteareth-25 | 2.0% |
| Tartaric Acid | 0.001% |
| DI Water | 55.389% |
| TOTAL | 100% |

Example 2c

Cream Composition

| Ingredient | Weight Percent |
|---|---|
| Phenylepherine | 0.5% |
| Oxymetazoline hydrochloride | 0.5% |
| Phenoxyethanol | 0.8% |
| Methylparaben | 0.2% |
| Propylparaben | 0.05% |
| Disodium EDTA | 0.01% |
| Butylated Hydroxytoluene | 0.05% |
| PEG-300 | 4.0% |
| PEG-6 Stearate (and) Glycol Stearate (and) PEG-32 Stearate | 7.5% |
| Cetostearyl alcohol | 4.0% |
| Caprylic capric triglycerides | 7.0% |
| Diisopropyl adipate | 7.0% |
| Oleyl alcohol | 7.0% |
| Lanolin USP | 2.0% |
| Ceteareth-6 (and) Stearyl Alcohol | 2.0% |
| Ceteareth-25 | 2.0% |
| Tartaric Acid | 0.001% |
| DI Water | 55.389% |
| TOTAL | 100% |

Example 3a

Ointment Composition

| Ingredient | Weight Percent |
|---|---|
| Metaraminol hydrobromide | 5.0% |
| Cholesterol | 3.0% |
| Stearyl Alcohol | 3.0% |

-continued

| Ingredient | Weight Percent |
| --- | --- |
| White Wax | 8.0% |
| White Petroleum | 76.0% |
| TOTAL | 100% |

Example 3b

Ointment Composition

| Ingredient | Weight Percent |
| --- | --- |
| desglymidodrine | 5.0% |
| Cholesterol | 3.0% |
| Stearyl Alcohol | 3.0% |
| White Wax | 8.0% |
| White Petroleum | 76.0% |
| TOTAL | 100% |

Example 3c

Ointment Composition

| Ingredient | Weight Percent |
| --- | --- |
| midodrine | 5.0% |
| Oxymetazoline | 5.0% |
| Cholesterol | 3.0% |
| Stearyl Alcohol | 3.0% |
| White Wax | 8.0% |
| White Petroleum | 76.0% |
| TOTAL | 100% |

Example 4a

Aqueous Solution

An aqueous solution of the invention includes brimonidine tartrate (0.07 wt %); Purite® (0.005%) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 4b

Aqueous Solution

An aqueous solution of the invention includes oxymetazoline hydrochloride (0.07 wt %); Purite® (0.005%) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

Example 4c

Aqueous Solution

An aqueous solution of the invention includes desglymidodrine (0.07 wt %); tetrahydrozoline hydrochloride (0.07 wt %); Purite® (0.005%) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

We claim:

1. A method of reducing cutaneous facial flushing associated with systemic use of phosphodiesterase type 5 inhibitors to treat erectile dysfunction in a human,
the method comprising topically administering to the facial skin affected by the cutaneous facial flushing of the human a composition comprising
a pharmaceutically active compound comprising
brimonidine or a pharmaceutically acceptable salt thereof; and
optionally, at least one alpha adrenergic receptor agonist selected from the group consisting of oxymetazoline, tetrahydrozoline, nephazoline, xylometazoline, phenylepherine, methoxamine, mephentermine, metaraminol, desglymidodrine, midodrine, pharmaceutically acceptable salts thereof, and any combination of such agonists and salts; and
a topically acceptable carrier,
in an amount effective to reduce the cutaneous facial flushing.

2. The method according to claim 1, wherein the alpha adrenergic receptor agonist is oxymetazoline, or pharmaceutically acceptable salts thereof.

3. The method according to claim 1, wherein the composition comprises brimonidine or a pharmaceutically acceptable salt thereof; or a combination of brimonidine or a pharmaceutically acceptable salt thereof and oxymetazoline or a pharmaceutically acceptable salt thereof; and
contains no other pharmaceutically active compound for reducing cutaneous facial flushing associated with systemic use of phosphodiesterase type 5 inhibitors.

4. The method according to claim 1, wherein the composition comprises brimonidine or a pharmaceutically acceptable salt thereof; or a combination of brimonidine or a pharmaceutically acceptable salt thereof and tetrahydrozoline or a pharmaceutically acceptable salt thereof; and contains no other pharmaceutically active compounds.

5. The method according to claim 1, wherein the alpha adrenergic receptor agonist comprises oxymetazoline hydrochloride.

6. The method according to claim 1, wherein the composition comprises brimonidine tartrate.

7. A method of reducing cutaneous facial flushing associated with systemic use of phosphodiesterase type 5 inhibitors to treat erectile dysfunction in a human, the method comprising topically applying a pharmaceutically active composition to facial skin affected by the cutaneous facial flushing of the human, the pharmaceutically active composition comprising:
i) an ingredient effective to reduce the cutaneous facial flushing, the ingredient consisting of brimonidine and/or a pharmaceutically acceptable salt thereof, and oxymetazoline and/or a pharmaceutically acceptable salt thereof, in an effective amount, and ii) a topically acceptable carrier.

8. A method of reducing cutaneous facial flushing associated with systemic use of phosphodiesterase type 5 inhibitors to treat erectile dysfunction in a human, the method comprising topically applying a pharmaceutically active composition to facial skin affected by the cutaneous facial flushing of the human, the pharmaceutically active composition comprising:

i) an ingredient effective to reduce the cutaneous facial flushing, the ingredient consisting of brimonidine and/or a pharmaceutically acceptable salt thereof, in an amount effective to reduce the cutaneous facial flushing, and iii) a topically acceptable carrier.

* * * * *